(12) United States Patent
Chan et al.

(10) Patent No.: US 7,393,437 B2
(45) Date of Patent: Jul. 1, 2008

(54) PHOTOCHEMICALLY CROSSLINKED COLLAGEN SCAFFOLDS AND METHODS FOR THEIR PREPARATION

(75) Inventors: Barbara P Chan, Hong Kong (CN); Kwok Fai So, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 11/225,108

(22) Filed: Sep. 14, 2005

(65) Prior Publication Data
US 2006/0099268 A1    May 11, 2006

Related U.S. Application Data

(60) Provisional application No. 60/609,600, filed on Sep. 14, 2004.

(51) Int. Cl.
    B01J 19/12    (2006.01)
    C08H 1/00     (2006.01)
    C08H 1/06     (2006.01)
    A61K 38/39    (2006.01)

(52) U.S. Cl. .............................. 204/157.61; 204/157.68; 424/422; 424/456; 424/484; 530/356

(58) Field of Classification Search ............ 204/157.68; 530/356; 430/270.1; 424/422, 456, 484
See application file for complete search history.

(56) References Cited

U.S. PATENT DOCUMENTS

| | | | | |
|---|---|---|---|---|
| 4,604,788 | A | * | 8/1986 | Boos ......................... 29/25.03 |
| 5,147,514 | A | * | 9/1992 | Mechanic .............. 204/157.68 |
| 5,256,418 | A | | 10/1993 | Kemp et al. |
| 5,718,012 | A | | 2/1998 | Cavallaro |
| 5,817,153 | A | | 10/1998 | Pendl et al. |

OTHER PUBLICATIONS

Adams, et al. "Crosslink Formation in Porcine Valves Stabilized by Dye-Mediated Photooxidation", J. Biomed. Mater. Res., 57(4):582-587 (2001).
Billiar, et al., "Effects of Carbodiimide Crosslinking Condition on the Physical Properties of Laminated Intestinal Submucosa", J. Biomed. Mater. Res.,56(1):101-8 (2001).
Moore, et al. "Stabilization of Pericardial Tissue by Dye-Mediated Photooxidation", J. Biomed. Mater. Res., 28(5):611-618 (1994).
Pitts, et al., "New Photoactivators for Multiphoton Excited Three-Dimensional Submicron Cross-Linking of Proteins: Bovine Serum Albumin and Type I Collagen", Photochem. Photobiol., 76(2):135-144 (2002).
Simmons, et al., "Evaluation of Collagen Cross-Linking Techniques for the Stabilization of Tissues Matrices", Biotechnol. Appl. Biochem. 17 (Pt 1):23-29 (Feb. 1993).
Weadock, et al., "Physical Crosslinking of Collagen Fibers: Comparison of Ultraviolet Irradiation and Dehydrothermal Treatment", J. Biomed. Mater. Res., 29(11):1373-79 (1995).

Balasubramanian D., Du, X., and Zigler, J.S. Jr., "The reaction of singlet oxygen with proteins, with special reference to crystallins", Photochemistry and Photobiology, 52(4):761-8 (1990).
Chan, B.P. and So, K.-F., "Photochemical crosslinking improves the physicochemical properties of collagen scaffolds", J. Biomed. Mater. Res., 75A:689-701 (2005).
Gelman, R.A., Williams, B.R. and Piez, K.A., "Collagen fibril formation—Evidence for a multistep process", J. Biol. Chem., 254(1):180-186 (1979).
Webster, A., Britton, D., Apap-Bologna, A. and Kemp, G., "A Dye-Photosensitized Reaction That Generates Stable Protein-Protein Crosslinks", Analytical Biochem., 179(1):154-7 (1989).
Li, Shu-Tung, "Biologic Biomaterials: Tissue-Derived Biomaterials (Collagen)", The Biomedical Engineering Handbook, 2nd ed., CRC Press LLC, Ch. 42, pp. 42-1 to 42-23 (2000).
Lee, Chi H., Singla, Anuj, Lee, Yugyung, "Biomedical applications of collagen", Int. J. Pharmaceutics, 221:1-22 (2001).
Yannas, Ioannis V., "Natural Materials", Biomaterials Sciences—An introduction to materials in medicine, Academic Press, pp. 84-94 (1996).
Kahn, Mark L., "Platelet-Collagen Responses: Molecular Basis and Therapeutic Promise", Semin. Thromb. Hemost., 30(4):419-25 (2004).
Abela, George S., Hage-Korban, Elie E., Tomaru, Takanobu, Barbeau, Gerald R., Abela, Oliver G., Friedel, Stephan E., "Vascular Procedures That Thermo-Coagulate Collagen Reduce Local Platelet Deposition And Thrombus Formation: Laser And Laser-Thermal Versus Balloon Angioplasty", Lasers Surg. Med., 29(5):455-63 (2001).
Kirchhofer, Daniel, Tschopp, Thomas B., Steiner, Beat, Baumgartner, Hans R., "Role of Collagen-Adherent Platelets in Mediating Fibrin Formation in Flowing Whole Blood", Blood, 86(10):3815-3822 (1995).
Tomizawa, Yasuko, "Clinical benefits and risk analysis of topical hemostats: a review", J. Artif. Organs, 8(3):137-142 (2005).
Aziz, O., Athanasiou, T., Darzi, A., "Haemostasis Using a Ready-to-Use Collagen Sponge Coated with Activated Thrombin and Fibrinogen", Surg. Technol. Int., 14:35-40 (2005).
Ramshaw, John A.M., Glattauer, Veronica, and Werkmeister, Jerome A., "Stabilization of Collagen in Medical Devices", Biomaterials and Bioengineering Handbook, Ch. 32, pp. 717-738 (2000).
Charulatha, V., and Rajaram, A., "Influence of different crosslinking treatments on the physical properties of collagen membranes", Biomaterials, 24(5):759-767 (2003).
Khor, Eugene, "Methods for the treament of collagenous tissues for bioprostheses", Biomaterials, 18(2):95-105 (1997).
Itoh, Soichiro, Takakuda, Kazuo, Kawabata, Sigenori, Aso, Yu, Kasai, Kanae, Itoh, Hiroshi, and Shinomiya, Kenichi, "Evaluation of cross-linking procedures of collagen tubes used in peripheral nerve repair", Biomaterials, 23(23):4475-4481 (2002).

(Continued)

Primary Examiner—Nashaat T. Nashed
Assistant Examiner—Marsha Tsay
(74) Attorney, Agent, or Firm—Pabst Patent Group LLP

(57) ABSTRACT

A method for producing collagen-based scaffolds with improved characteristics, which broadens the usage of collagen in tissue engineering and the products so produced are described. The method comprises reconstitution of three-dimensional collagen matrices from collagen monomer solution and crosslinking the matrix with a light source in the presence of a photosensitizing reagent. The crosslinked products can be in any shape and form and used in the dry or wet state, for applications including but not limited to tissue engineering and controlled drug delivery.

26 Claims, 10 Drawing Sheets

OTHER PUBLICATIONS

Pieper, J.S., Oosterhof, A., Dijkstra, P.J., Veerkamp, J.H., and Van Kuppevelt, T.H., "Preparation and characterization of porous crosslinked collagenous matrices containing bioavailable chondroitin sulphate", *Biomaterials*, 20(9):847-858 (1999).

Henderson, Barbara W. and Dougherty, Thomas J., "How Does Photodynamic Therapy Work?", *Photochem. Photobiol.*, 55(1):145-157 (1992).

Mulroy, Louise, Kim, June, Wu, Irene, Scharper, Philip, Melki, Samir A., Azar, Dimitri T., Redmond, Robert W., and Kochevar, Irene E., "Photochemical Keratodesmos for Repair of Lamellar Corneal Incisions", *Invest. Ophthalmol. Vis. Sci.*, 41(11):3335-40 (2000).

Chan, Barbara P., Kochevar, Irene E., and Redmond, Robert W., "Enhancement of Porcine Skin Graft Adherence Using a Light-Activated Process", *J. Surg. Res.*, 108(1):77-84 (2002).

Chan, Barbara P., Amann, Christopher, Yaroslavsky, Anna N., Title, Craig, Smink, David, Zarins, Bertram, Kochevar, Irene E., and Redmond, Robert W., "Photochemical Repair of Achilles Tendon Rupture in a Rat Model", *J Surg. Res.*, 124:274-279 (2005).

Ramshaw, John A.M., Stephens, Laurie J., and Tulloch, Peter A., "Methylene blue sensitize photo-oxidation of collagen fibrils", *Biochim. Biophys. Acta*, 1206(2):225-230 (1994).

Yeh, Alvin T., Choi, Bernard, Nelson, Stuart J., and Tromberg, Bruce J., "Reversible Dissociation of Collagen in Tissues", *J. Invest. Dermatol.*, 121(6):1332-5 (Dec. 2003).

Star, Willem M., "Light dosimetry in vivo", *Physics in Medicine & Biology*, 42(5):763-787 (May 1997).

Niemz, Markolf H., *Laser-Tissue Interactions: Fundamental and Applications*, 3rd, enlarged ed., Springer-Verlag Berlin Heidelberg New York, pp. 17-18 & 68-76 (2004).

Jacquez, John A. and Kuppenheim, Hans F., "Theory of the Integrating Sphere", *J. Opt. Soc. Am.*, 45(6):460-470 (1955).

Yaroslavsky, I.V., Yaroslavsky, A.N., Goldbach, T., and Schwarzmaier, H.-J., "Inverse hybrid technique for determining the optical properties of turbid media from integrating-sphere measurements", *Applied Optics*, 35(34):6797-6809 (Dec. 1, 1996).

Yaroslavsky, A.N., Yaroslavsky, I.V., Goldbach, T., and Schwarzmaier, H.-J., "Influence of the Scattering Phase Function Approximation on the Optical Properties of Blood Determined from the Integrating Sphere Measurements", *J. Biomed. Opt.*, 4(1): 47-53 (Jan. 1999).

Yaroslavsky, A.N., Schulze, P.C., Yaroslavsky, I.V., Schober, R., Ulrich, F., and Schwarzmaier, H.-J., "Optical properties of selected native and coagulated human brain tissues in vitro in the visible and near infrared spectral range", *Phys. Med. Biol.*, 47:2059-2073 (2002).

Pickering, John W., Moes, Christian J.M., Sterenborg, H.J.C.M., Prahl, Scott A. and Van Gemert, Martin J.C., "Two integrating spheres with an intervening scattering sample", *J. Opt. Soc. Am. A*, 9(4):621-631 (Apr. 1992).

Pickering, John W., Prahl, Scott A., Van Wieringen, Niek, Beek, Johan F., Sterenborg, Henricus J.C.M. and Van Gemert, Martin J.C., "Double-integrating-sphere system for measuring the optical properties of tissue", *Applied Optics*, 32(4):399-410 (1993).

Prahl, Scott A., "Light Transport in Tissue", Ph.D. Thesis, U. of Texas at Austin (Dec. 1988).

Elliot, Dawn M. and Sarver, Joseph J., "Young Investigator Award Winner: Validation of the Mouse and Rat Disc as Mechanical Models of the Human Lumbar Disc", *Spine*, 29(7):713-22 (2004).

Lin, Chia-Wen and Lin, Jui-Che, "Surface characterization and platelet compatibility evaluation of surface-sulfonated chitosan membrane", *J. Biomater. Sci. Polymer Edn.*, 12(5):543-57 (2001).

Du, Hai, Fuh, Ru-Chun Amy, Li, Junzhong, Corkan, Andrew and Lindsey, Jonathan S., "Technical and Software Note—PhotochemCAD: A Computer-Aided Design and Research Tool in Photochemistry", *Photochemistry and Photobiology*, 68(2):141-142 (1998).

Kochevar, Irene E., "Principles of Photobiology", *Topics In Clinical Dermatology—Photosensitivity*, Igaku-Shoin Medical Publishers, Inc., Ch. 2, pp. 9-24 (1992).

Kochevar, Irene E. and Redmond, Robert W., "Photosensitized Production of Singlet Oxygen", *Methods in Enzymology—vol. 319—Singlet Oxygen, UV-A, and Ozone*, Academic Press, vol. 319, pp. 20-28 (2000).

Lansche, Richard K., "Vital Staining in Normal Eyes and In Keratoconjunctivitis Sicca", *Am. J. Ophthalmol.*, 60:520-5 (1965).

Grewal, Rupinder, Xu, Jiangming, Sotereanos, Dean G. and Woo, Savio L-Y., "Biomechanical Properties of Peripheral Nerves", *Hand Clinics*, 12(2):195-204 (May 1996).

Zdrahala, Richard J., "Small Caliber Vascular Grafts. Part. I: State of the Art", *J. Biomater. Appl.*, 10:309-329 (1996).

He, Wei, Yong, Thomas, Teo, Wee Eong, Ma, Zuwei and Ramakrishna, Seeram, "Fabrication and endothelialization of Collagen-Blended Biodegradable Polymer Nanofibers: Potential Vascular Graft for Blood Vessel Tissue Engineering", *Tissue Eng.*, 11(9-10):1574-88 (2005).

Clemetson, Kenneth J., Clemetson, Jeannine M., "Platelet Collagen Receptors", *Thromb. Haemost.*, 86(1):189-97 (Jul. 2001).

Douven, Lucien F.A. and Lucassen, Gerald W., "Retrieval of optical properties of skin from measurement and modeling the diffuse reflectance", *Proc. SPIE*, 3914:312-323 (Jun. 2000).

Ritz, Joerg-P., Roggan, Andre, Isbert, Christoph, Muller, Gerhard, Buhr, Heinz J. and Germer, Christoph-T., "Optical Properties of Native and Coagulated Porcine Liver Tissue Between 400 and 2400nm", *Lasers Surg. Med.*, 29:205-12 (2001).

Zhu, Timothy C., Dimofte, Andreea, Finlay, Jarod C., Stripp, Diane, Busch, Theresa, Miles, Jeremy, Whittington, Richard, Malkowicz, S. Bruce, Tochner, Zelig, Glatstein, Eli and Hahn, Stephen M., "Optical Properties of Human Prostate at 732 nm Measured In Vivo During Motexafin Lutetium-mediated Photodynamic Therapy", *Photochem. Photobiol.*, 81:96-105 (2005).

Vargas, Gracie, Chan, Kin F., Thomsen, Sharon L. and Welch, A.J., "Use of Osmotically Active Agents to Alter Optical Properties of Tissue: Effects on the Detected Fluorescence Signal Measured Through Skin", *Lasers Surg. Med.*, 29:213-20 (2001).

Chan, B.P., So, K.F. "Photochemical crosslinking affects the microstructure of porous collagen scaffolds", The 8th TESI Annual Meeting of Tissue Engineering Society International, Oct. 22-25, 2005, Shanghai, P.R. China, Abstract No. 476 (2005).

\* cited by examiner

Fig. 5

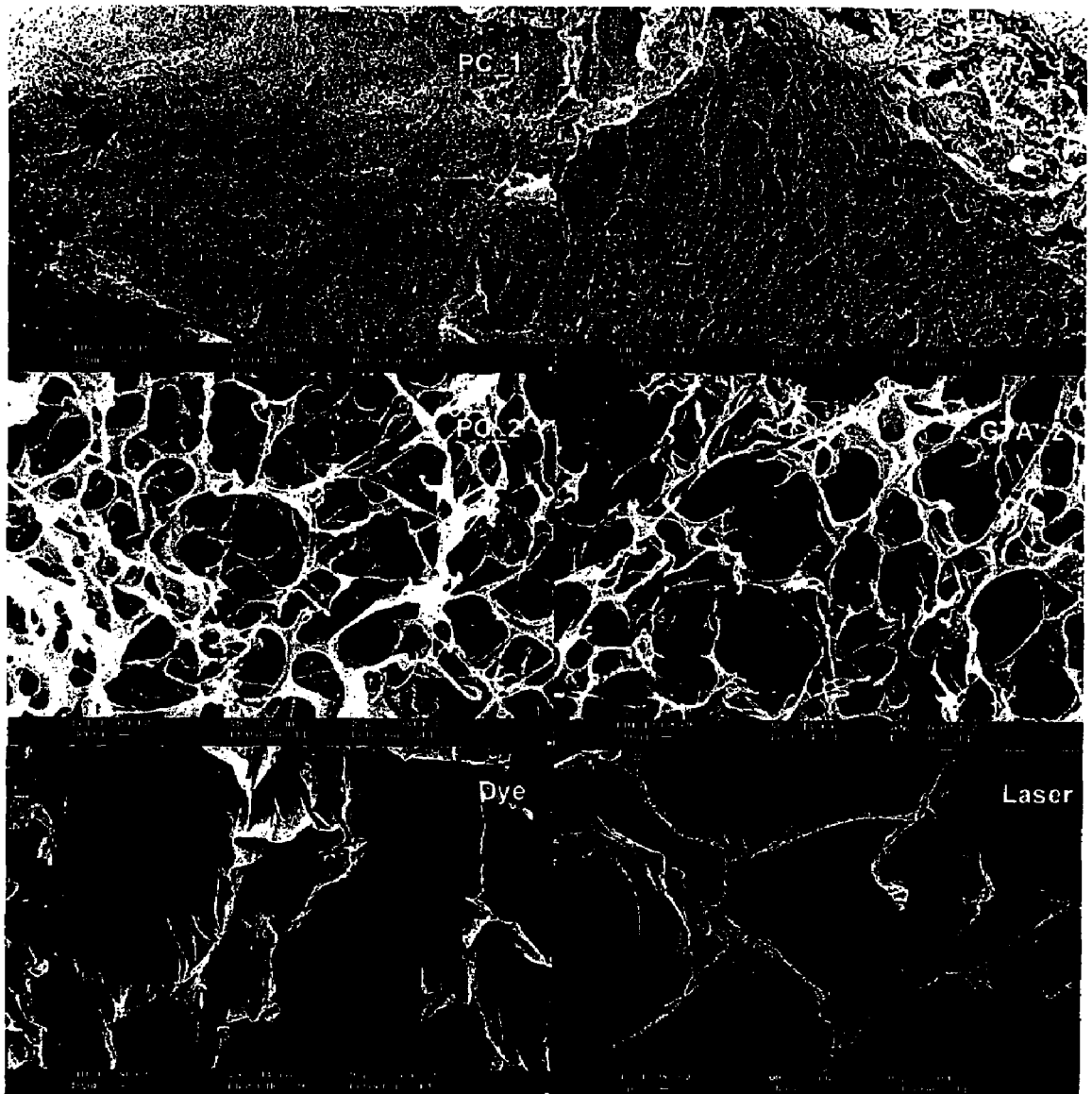

Fig. 5 – SEM pictures of porous collagen scaffolds in different treatment groups. PC_1: photochemically crosslinked; GTA_1: glutaraldehyde (chemically) crosslinked; Dye: dye control group; Laser: laser control group; Control: untreated control group (Magnification: 200X); PC_2: Photochemically crosslinked at high magnifications; GTA_2: chemically crosslinked at high magnifications (8KX).

PHOTOCHEMICALLY CROSSLINKED COLLAGEN SCAFFOLDS AND METHODS FOR THEIR PREPARATION

CROSS-REFERENCES TO RELATED APPLICATION

This non-provisional application claims the benefit of priority to U.S. provisional application 60/609,600 filed Sep. 14, 2004.

STATEMENT REGARDING FEDERALLY SPONSORED RESEARCH OR DEVELOPMENT

Not Applicable.

REFERENCE TO SEQUENCE LISTING

Not Applicable.

BACKGROUND OF THE INVENTION (1) Field of the Invention

The present invention relates generally to crosslinked collagen scaffolds. More particularly, it relates to the method of crosslinking and producing collagen-based scaffolds with improved properties using light and photosensitizing reagent, and to the products produced by the method.

(2) Description of Related Art

Collagen is the most abundant protein in the extracellular matrix of human tissue and plays important roles in providing structural support as well as performing other functions in tissue growth and regeneration. Apart from collagen, other types of extracellular matrix components such as proteoglycans, elastin, etc. also play important roles in maintaining tissue structure and function. Producing scaffolds simulating natural tissue is an essential enabling technology in the tissue engineering industry.

Collagen is the best natural biomaterial for tissue engineering because of its close resemblance to nature, and its negligible immunogenecity and excellent biocompatibility. However, unprocessed collagen usually has insufficient mechanical properties for it to be useful in engineering tissues in particular the weight-bearing tissues such as tendons, ligaments, intervertebral discs, etc. Unprocessed collagen is also difficult to manipulate and put sutures through during the implantation process. Further, unprocessed collagen is highly water swellable and is vulnerable to enzymatic digestion and thermal denaturation.

Crosslinking has been used to improve the properties of collagen and therefore is crucial in the tissue engineering industry. Tissue engineering companies have disclosed various methods for crosslinking collagen constructs and scaffolds using chemical methods such as treatment with glutaraldehyde (Cavallaro, U.S. Pat. No. 5,718,012 for "Method of Strength Enhancement of Collagen Constructs") and physical methods such as lyophilization (Kemp et al., U.S. Pat. No. 5,256,418 for "Collagen Constructs") to enhance the strength and stability of the structures. Other physical crosslinking methods such as ultraviolet (UV) and gamma irradiation and dehydrothermal treatment have also been reported.

However, both chemical and physical crosslinking methods have encountered problems. Chemical crosslinking of collagen using a reagent such as glutaraldehyde, although efficient, compromises the biocompatibility of scaffolds because the toxic residual chemicals and degradation products induce cytotoxicity and calcification (Simmons D. M. et al., "Evaluation of Collagen Cross-Linking Techniques for the Stabilization of Tissue Matrices", *Biotechnol Appl Biochem.* 17 (Pt 1):23-9 (1993)). Physical crosslinking methods are time-consuming (Weadock K. S. et al., "Crosslinking of Collagen Fibers: Comparison of Ultraviolet Irradiation and Dehydrothermal Treatment", *J Biomed Mater Res.* 29(11): 1373-9 (1995); and Billiar K. et al., "Effects of Carbodiimide Crosslinking Conditions on the Physical Properties of Laminated Intestinal Submucosa", *J. Biomed Mater Res.* 56(1): 101-8 (2001)), and compromise the stability of scaffolds because UV and gamma irradiation, and the harsh processing conditions in the dehydrothermal treatment method denature the protein (Weadock et al., supra; Billiar et al., supra). As a result, a long-felt need has existed for alternative methods of enhancing the physico-chemical properties of collagen coupled with features such as rapid and efficient processing, nil toxic substances, non-thermal processing and absence of denaturation of collagen.

Previous studies involving light-activated processes to stabilize xenografts (heterografts) such as pericardial tissues, and heart values for transplantation have been reported (Adams A. K. et al., "Crosslink Formation in Procine Valves Stabilized by Dye-Oxidated Photooxidation", *J. Biomed Mater Res*, (57):582-587 (2001); Moore M. A. et al., "Stablization of pericardial tissue by dye-mediated photooxidation", *J. Biomed Mater Res*, 28(5):611-618 (1994)). These studies were aimed at further stabilizing intact tissues having extracellular matrix protein networks and the intrinsic mechanical properties thereof. The xenograft repair approach differs greatly from that used in tissue engineering, in which tissue-like scaffold structures are built from basic units such as extracellular matrix components, cells and growth-stimulating bioactive factors.

Studies on the crosslinking of collagen proteins in solution using light-activated processes have been reported (Pitts J. D. et al., "New Photoactivators for Multiphoton Excited Three-Dimensional Submicron Cross-Linking of Proteins: Bovine Serum Albumin and Type I Collagen", *Photochem., Photobiol* 76(2): 135-144). The average laser power used to create submicron structures ranged up to $10^{10}$ W/cm². Although there was no evidence as to whether the collagen was denatured and whether the processed collagen structures have improved strength and stability, at such high power, collagen protein is very likely to coagulate and become denatured. Therefore, the crosslinking is based on thermal mechanism.

Mechanic, U.S. Pat. No. 5,147,514 for "Process for Crosslinking Collagenous Material and Resulting Products" describes a photooxidative process for crosslinking proteins using photocatalysts in the presence of oxygen. This patent discloses the oxygen dependence of the crosslinking process in that bubbling of air or oxygen, or stirring the reaction mixture vigorously was used to increase the concentration of oxygen. Further, a photocatalyst was used so that the compound did not change before and after the process. This is not the case for the photochemical crosslinking process of the present invention in that the photosensitive reagent participates in the crosslinking process. Moreover, the prior art crosslinking process does not strengthen or stiffen the crosslinked products and therefore cannot solve the major problem, namely, the inadequate mechanical properties of unprocessed collagen used as scaffolds for tissue engineering. Further, the patent does not reveal any intention to produce larger and thicker scaffolds. The thickness of collagen scaffolds to be crosslinked by irradiation is limited because of the depth of penetration of the light source.

SUMMARY OF THE INVENTION

The present invention provides a method for producing crosslinked collagen and composites scaffolds with enhanced properties such as strength and stability and maintains excellent biocompatibility. The method comprises (a) reconstitution of three-dimensional collagen extracellular matrix from collagen monomer solution using methods such as raising the pH of the solution for certain period of time; (b) cross-linking at least a portion of the matrix contacting it with a photosensitizing reagent at a particular concentration in darkness for certain period of time before or after reconstitution; (c) removing excess photosensitizing reagent; (d) irradiation of the scaffolds with a light source of sufficient energy for a certain period of time so as to form crosslinked scaffolds; and (e) dehydration of the crosslinked scaffolds. The method of the invention can further comprise laminating the rehydrated and crosslinked scaffolds for multiple times to produce large scaffolds. The method of the invention also enables incubation with other extracellular matrix component for making composites scaffolds and immobilization of bioactive factors or drugs that can be subsequently released from the scaffolds.

The collagen monomers can be of different collagen phenotypes including collagen type I, II, III and preferably type I, II, III which are abundant in human tissues. The collagen monomers can be isolated or extracted from various animal sources including but are not limited to rat tail, bovine Achilles tendon, porcine skin, human placenta. The collagen monomers can be from different fractions of collagen extraction from animal sources including but not limited to the acid-soluble fraction, pepsin digested fraction, or the insoluble fraction.

The reconstitution of collagen monomer solution can be induced by methods such as raising the pH of the solution, increasing the temperature of the solution and immersion in solutions with high ionic strength. The collagen reconstitution is induced preferably by raising the pH of the solution by exposing the solution in a chamber filled with an alkaline vapor or solution, preferably ammonia, for a period ranging from 3 minutes to 96 hours. The collagen monomer solution can be exposed to an alkaline solution, preferably ammonia water, through a semi-permeable membrane, including but are not limited to dialysis tubing, cellulose membrane, filter paper, etc., with a cut-off size smaller than collagen molecules.

If an alkaline solution-containing chamber is used to initiate reconstitution, the collagen monomer solution is sealed in a semipermeable membrane or its equivalent and immersed in alkaline solution such as ammonia water.

The photosensitizing reagent includes but is not limited to fluorescein, rose Bengal, methylene blue, eosin, and porphyrins. The concentration of the photosensitizing reagent varies from 0.000001% to 10%. The matrix is brought into contact with the photosensitizing reagent for a period ranging from 5 seconds to 100 hours before or after reconstitution. The excess photosensitizing reagent can be removed by multiple rinsing in water or isotonic solution.

The light source can be a UV or visible source, such as a laser, xenon light, light-emitting diode (LED), etc. The light source can be used to irradiate the scaffolds at an irradiance which varies from 0.0001 W/cm2 to 10 W/cm2. The mode of irradiation can be pulsed or continuous. The energy used for irradiation ranges from 0.0001 J to 10000 J. The period of irradiation ranges from 5 seconds to 100 hours.

The scaffolds can be placed in a container provided with a cooling means such as running cold water. The scaffolds are removed from the solution containing the photosensitizing reagent and rinsed several times in distilled water or isotonic solution prior to irradiation. The scaffolds are irradiated without bubbling air or oxygen into the reaction mixture or vigorous stirring.

The dehydration can be via air-drying, freeze-drying, vacuum drying, critical point drying, alcohol drying, acetone drying, centrifugation and compression against water absorbents and the like.

The invention is able to strengthen the scaffolds by imparting to them improved stress-strain relationship (FIG. 2) and thus enhanced mechanical and structural properties such as the peak load, ultimate stress, rupture strain and tangent moduli (FIGS. 3 & 4) so that they can be used for tissue engineering purposes where a better mechanical property is required.

The invention also enables the formation of collagen scaffolds with fine microstructures with micron-sized pores and nano-sized fibers simulating that of the chemically crosslinked ones while the uncrosslinked scaffolds only have membrane-like macrostructures (FIG. 5). The size of the pores is dependent on various factors including but are not limited to the concentration of the photosensitizing dyes (FIG. 6) and the light dosimetry (FIG. 7). Therefre, collagen scaffolds of fine microstructure can be fabricated for different tissue engineering purposes. Since collagen is a good natural biomaterials with excellent biocompatibility that enhances the cellular interaction and growth, crosslinked collagen scaffolds of the present invention can also be used as a filler material of other biomaterials with macrostructures such as PLGA so as to enhance the biocompatibility of that biomaterials.

The method is able to chemically stabilize the scaffolds with better thermostability in terms of much higher denaturation or solubilization point than the uncrosslinked form in that the crosslinked scaffolds still retained the well-organized three-dimensional structure while the uncrosslinked ones are solubilized or melt at the end of thermal challenge due to the breakdown of the inter- and intra-molecular linkages. (FIGS. 8 & 9)

The method is able to chemically stabilize the scaffolds with improved resistance to in vitro biodegradability (e.g. collagenase digestion) (FIG. 10) and therefore can prolong the life span of the scaffolds following implantation. Crosslinked collagen scaffolds have been found intact and stable without foreign body reactions and inflammation as long as 6 months post implantation in subcutaneous pockets in rats (FIG. 11) indicating its excellent tissue compatibility. Crosslinked collagen scaffolds also maintains excellent biocompatibility for cell growth that fibroblasts were able to adhere and grow on the scaffolds in a similar manner to the uncrosslinked controls (FIG. 15).

The method also reduced the intrinsic thrombogenecity of collagen membranes in that the number of platelet adhesion was reduced significantly and the thrombin activation was completely prevented as compared with the uncrosslinked membranes (FIG. 16) indicating that the crosslinked collagen scaffolds are suitable for vascular tissue engineering such as making small diameter blood vessels.

The method of the invention reduces the swelling ratio of the scaffolds while gradually increasing the swelling ratio in a time-dependent manner. The effect can be controlled by varying factors such as the dosimetry of the light source such as the fluence (FIG. 12) and the concentration of the photosensitizing agent (FIG. 13). The swelling ratio is an indication for the extent of crosslinking and the higher the swelling ratio the faster the release of any molecules immobilized.

The photochemical reagent to be used and its concentration are the key controlling variables for the process.

The light source to be used and its fluence and irradiance are another key controlling variables for the process.

The status of the biomaterials, either in solution form, or reconstituted gel form, or rehydrated biomaterials, to be used for crosslinking, affect the properties of the scaffolds. The presence of other small molecules able to be the crosslinkers such as pyridinoline also affect the resultant properties of the materials.

The concentration of the collagen monomer or other extracellular matrix components also affects the resultant properties.

The method affords a way to laminate layers of scaffolds, in particular, laminating the crosslinked products with the collagen monomer solution during reconstitution and is followed by repeating the method.

The method is able to produce three-dimensional structures of appropriate thickness, ranging from 50 μm to theoretically unlimited thickness with enhanced mechanical properties such as compression moduli (FIG. 14) for different tissue engineering purposes. The products produced thereby can be in any shape and form, including but not limited to membranes, sheets, blocks, foams, tubules, discs, fibers, etc. The method is able to crosslink the collagen scaffolds at selective sites by methods including but not limited to modifying the light source so that the spot size and beam only reach the selective sites, thus controlling the sites to where the photosensitizing reagent is delivered.

The photochemical crosslinking method described and claimed herein is able to produce collagen scaffolds and composites of different shapes, forms and dimensions, with enhanced strength, thermostability and resistance to proteolytic digestion, as well as reduced swelling ratio. Swelling ratio is the ratio of the difference between the wet and the dry weight of the scaffold to its dry weight. These scaffolds and composites are adapted to be delivered by methods such as implantation and injection, to repair or replace defective tissues including but not limited to tendons, ligaments, intervertebral discs, nerves, and blood vessels. The reduced swelling ratio and increased stability of the scaffolds also enables controlled release of molecules or drugs, which can be growth-stimulating, anti-inflammatory, hemostatic, etc, when they are immobilized in the scaffolds.

BRIEF DESCRIPTION OF THE DRAWINGS

FIG. 5 are magnified cross-sectional views of porous collagen scaffolds of different treatment groups prepared in accordance with the present invention. PC_1: photochemically crosslinked; GTA_1: glutaraldehyde (chemically) crosslinked; Dye: dye control group; Laser: laser control group; Control: untreated control group (Magnification: 200×); PC_2: Photochemically crosslinked at high magnifications; GTA_2: chemically crosslinked at high magnifications (8K×).

DETAILED DESCRIPTION OF THE INVENTION

Figure 1:
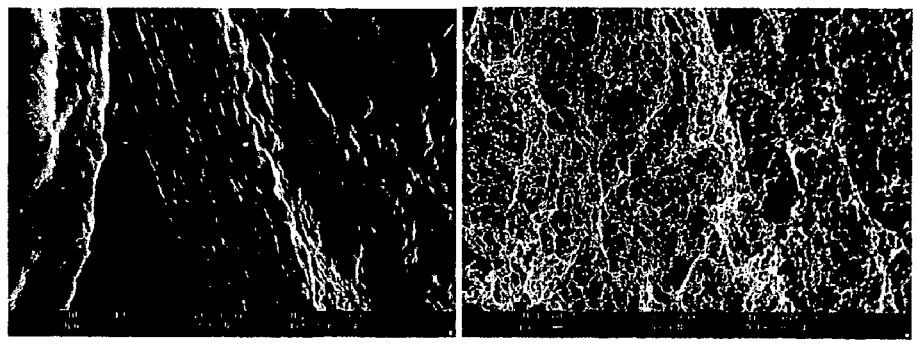
FIGS. 1A (magnification: 5K×) and 1B (magnification: 879×) are magnified cross-sectional views of a non-porous and porous collagen scaffolds, respectively prepared according to the present invention.

The present invention enables the production of collagen scaffolds, in different shapes, forms and sizes, with improved properties such as enhanced strength, thermostability, resistance to proteolytic digestion, reduced swelling ratio, improved haematocompatibility and excellent biocompatibility. Collagen scaffolds with enhanced strength are useful in providing structural and functional supports in engineered tissues, particularly weight-bearing tissues such as tendons, ligaments, intervertebral discs and the like. Collagen scaffolds with enhanced chemical and thermal stability are less vulnerable to denaturation or destabilization during other processing such as sterilization. Collagen scaffolds with increased resistance to proteolytic digestion and chemical stability are less vulnerable to disintegration in physiological and proteolytic environments upon implantation at the repair site and therefore have longer life span to allow better tissue growth and regeneration. Crosslinked collagen scaffolds with good cell and tissue compatibility prevents unfavorable inflammatory events and enhances cell adhesion and growth and thus allows better tissue regeneration after implantation. Collagen scaffolds with improved haematocompatibility or reduced thromogenicity can be used in vascular tissue engineering that uncrosslinked collagen is inherently not suitable for making artificial blood vessels because it is known to be the most thrombogenic component of the extracellular matrix inducing platelet adhesion and thrombin activation upon contact with blood.

Collagen scaffolds have solid three-dimensional structures and are obtained from collagen monomers in solution form, isolated or extracted or prepared from any animal sources, such as rat tail, porcine skin, bovine Achilles tendon, and human placenta. The collagen monomers can be from different fractions during collagen extraction, acid-soluble, pepsin-soluble or insoluble. The collagen monomer solution is made into appropriate concentrations ranging from 0.1 to 100 mg/ml depending on the type of tissue to be built. Collagen monomer solution, preferably at a concentration of 1-10 mg/ml, degassed by methods such as centrifugation, is placed into a container, preferably an inert and non-adherent container made for a material including but not limited to glass, polystyrene, and silicone rubber. Any air bubbles generated during the process are removed by puncturing the air bubble with a sharp object such as a fine syringe needle. The collagen monomer solution is induced to reconstitute itself into collagen gel consisting of fibrils by methods including but not limited to pH change, preferably an increase from acidic pH to alkaline pH, temperature change, preferably an increase from 4° C. to 37° C., a change in ionic strength, by contact with a solution of high ionic strength. A preferred method is to use an alkaline chamber filled with ammonia vapor. The container with the collagen monomer solution is then placed into the chamber sealed for a period, of preferably 30 mins. The duration of exposure to the alkaline vapor is a factor affecting the mechanical properties of the collagen scaffolds. If a pH change is to be used to induce reconstitution of the membrane in a solution, a semi-permeable membrane or material is place at the interface between the alkaline solution and the collagen monomer solution or at the interface between an inner and an outer chamber as described in U.S. Pat. No. 5,256,418, supra. The colorless collagen monomer solution becomes opaque upon successful reconstitution.

The reconstituted collagen gel or scaffold is rinsed in distilled water or isotonic (physiological saline) solution to remove excess alkalinity. The collagen scaffold can form composite scaffolds with other extracellular matrix components including but not limited to other collagen subtypes and proteoglycans. If composite scaffolds are to be produced, extracellular matrix component other than collagen can be suspended in the collagen solution during reconstitution or the collagen gel is equilibrated with a solution containing the second extracellular matrix component at appropriate concentration for a certain period before photochemical crosslinking.

Collagen is also a good candidate for a drug delivery system, particularly of protein drugs because of its excellent biocompatibility, its interaction with the protein drug that protects the drug from disintegration, and the fact that it sometimes potentiates the bioactivities of drugs such as growth factors. However, collagen gel becomes highly swollen in water and uncrosslinked collagen is vulnerable to proteolytic digestion and disintegration upon implantation. Both swelling and disintegration are the mechanisms for drug release in the polymer network. As a result, drug molecules when immobilized within the collagen network, release rapidly without controlled release. This limits the applicability of collagen gel as a device to control the delivery of drugs, including but not limited to proteins, growth factors, antibiotics, and anti-inflammatory drugs. Controlling the matrix variables such as the concentration and density of collagen gel carriers, extent of crosslinking of the collagen gel, etc. enables one to exert control over the release pattern and the kinetics of drugs immobilized within the collagen network. The photochemical crosslinking method of the present invention has reduced the swelling ratio and increased the resistance of the collagen carrier to proteolytic disintegration and therefore has the potential to control the release of drugs.

Dehydration is an important mechanism for increasing the density of collagen scaffolds and is itself an efficient means for stabilizing and strengthening collagen scaffolds. The dehydration means employed greatly affect material and mechanical properties. Air-drying produces scaffolds with minimal levels of porosity (FIG. 1) and therefore maximal density and stability, wherein freeze-drying or lyohilization results in porous scaffolds (FIG. 1) with lower density and therefore lower strength and stability. Since many properties of the collagen scaffolds such as porosity, density, strength and stability, are dependent on the type of tissue to be built, the method for dehydration varies and building tissues with heterogenous structure and properties is feasible. An example is to produce a nerve conduit using the method disclosed in the present invention, with a nonporous dense collagen membrane as the epineurium through methods such as air-drying and vacuum drying and a highly porous collagen and proteoglycan-based semi-solid matrix as the endoneurium through methods such as lyophilization.

Photosensitizing reagents are chromophores able to be activated by photons at particular wavelengths, including but not limited to fluorescein, eosin, rose Bengal, and methylene blue. Photosensitizing reagents for use in the present invention include rose Bengal, which has a spectrum of absorption up to approximately 600 nm. Apart from the UV region, there are two absorption peaks at approximately 320 nm and 550 nm. Rose Bengal has high absorption efficiency and therefore is a very efficient photosensitizing reagent. Rose Bengal is a vital dye that has been used in clinical diagnostic for ophthalmologic diseases for decades (Lansche R. K., "Vital Staining in Normal Eyes and in Keratoconjunctivitis Sicca", *Am. J. Ophthalmol.* 60(3):520-5 (1965)). It is a safe reagent to use. Rose Bengal is a fluorescent photosensitizing reagent that is water soluble. However, aggregates may form at high concentration such as >1% (w/v) and therefore rose Bengal, preferably ranged from 0.00001% to 0.01% was used in the present invention. Rose Bengal solution was prepared in darkness using a solution such as distilled water, PBS and ethanol. Since photochemical crosslinking only occurs at sites where the substrates for crosslinking, the photosensitizing reagent and the light all present, by controlling the site where the photosensitizing reagent is present and where the light irradiates, the site for crosslinking can be selected. The rate of diffusion of rose Bengal solution in different biomaterials including collagen scaffolds is different and is proportional to the density of the materials and the concentration of the photosensitizing reagent. As a result, controlling the time of exposure of the collagen scaffolds to rose Bengal solution controls the site where photochemical crosslinking occurs. If the surface of the collagen scaffolds instead of the bulk materials is to be crosslinked, rose Bengal solution can be delivered through brushing or painting, or placing the surface for crosslinking of the collagen scaffold on top of a thin layer of absorbent, including but are not limited to kimwipe, tissue paper, cellulose membrane, filter paper, for a certain period of time. Or, it can be done by forming collagen layer by layer where the layers have different concentrations of photosensitizing reagent immobilized. Since the extent of crosslinking is dependent on the dose of the photosensitizing reagent, a gradient of crosslinking within the collagen scaffolds is also possible. Other methods of delivery of the photosensitizing reagent to the collagen scaffolds such as injection are possible. Excess photosensitizing reagent can be removed by blotting the collagen scaffolds on a dry absorbent material such as tissue paper or thorough rinsing in a diluent such as distilled water. The photosensitizing reagent can be brought into contact with collagen before and after reconstitution, or before and after dehydration of reconstituted scaffolds.

The materials are preferably maintained in darkness during the process. When excess reagent is removed by rinsing, the hydrated material will be brought to a light source, be it a UV source, a laser, LED or other source of visible light. The amount and power intensity of the light affect the extent of crosslinking as it is proportional to the number of photons. Suitable light sources for use in the present invention include an argon laser, at a wavelength of 514 nm, or multiline green laser. Other lasers which the rose Bengal absorbs can also be used. The spot size of the irradiation needs to be large enough to cover the material, or a scanning light source that is able to scan the material at controllable speed, or multiple light delivery devices such as optic fibers can be used to deliver light for crosslinking scaffolds with irregular shape. The argon laser useful in the present invention can be continuous or pulsed. The Ultima 2000 argon laser (Coherent Medical) generates laser pulses at 0.2 W with duration of 1 second. The total energy of light delivered to crosslink collagen scaffolds in the present presentation ranged from 12.5 J to 200 J and therefore 62.5 to 1000 pulses were delivered.

Light penetration has a limit of depth in all materials including collagen. An example is the degree of light penetration at a wavelength of around 500 nm in human fair skin, which is around 350 micrometer. See, Douven L. F., "Retrieval of Optical Properties of Skin From Measurement and Modeling the Diffuse Reflectance, *Proc. SPIE* 3914:312 (2000). Previous studies on the total transmittance of light at around 500 nm have shown that light can penetrate porcine skin dermis and bovine Achilles tendon to a depth of approximately 700 micrometers. Although light penetration should be better in reconstituted collagen gel compared to skin and tendon tissue, which have closely packed connective tissue networks and intrinsic chromophores such as melanin and haemoglobin, the limit of light penetration depth still restricts the thickness of scaffolds to be crosslinked and produced. The method disclosed in the present invention is able to solve this problem. Production of thick collagen scaffolds is enabled by (1) laminating the first crosslinked scaffold with the second layer during the reconstitution step where the monomer solution is gelated to form solid gel; (2) photochemically crosslinking the reconstituted collagen gel and laminating the two scaffold layers; (3) dehydrating the two scaffold layers together and (4) repeating the process multiple times until scaffolds of appropriate size are produced. Other methods such as modifying the optical properties of tissue or materials to be photochemically crosslinked such as immersing in glycerine solution as described in Pendl et al. U.S. Pat. No. 5,817,153 for "Method of Photo-Oxidative Treatment of Tissues Containing Collagen" can be used.

The whole process can be performed under sterile conditions in that the collagen monomer solution is sterile, the photosensitizing reagent is filtered by 0.22 micron filter or autoclaved, the ammonia chamber is prepared in a safety cabinet, and the light source is irradiated through a container with good transparency that is made of materials such as glass and polystyrene, etc. Or, the collagen scaffolds are preferably sterilized by alcohol treatment or other methods such as ethylene oxide gas treatment after production of the scaffolds but prior to implantation.

EXAMPLE 1

Fabrication of Collagen Scaffolds

An acid-soluble rattail collagen type I solution at a concentration of 4 mg/ml is degassed and 1.5 ml of it is carefully laid down onto a plastic container 1.5 cm in diameter, and any air bubbles generated are removed. The pH of the solution is raised by placing the solution in a chamber containing ammonia vapor for 30 minutes. Opague solid collagen gel is formed from colorless solution. A collagen matrix of approximately 7.5 mm thick and 15 mm diameter is obtained and then thoroughly rinsed with water. The gel is immersed in rose Bengal at a concentration ranging from 0.000078125% to 0.01% for 2 hours. Control collagen gel is immersed in water. Excess photosensitizing reagent is removed by thorough rinsing with water. Fully swollen collagen gel is then photochemically crosslinked by exposing it to an argon laser (Coherent Medical, Ultima 2000). Laser pulses of is duration and a power of 0.2 W were used. The total energy input was from 12.5 J to 200 J. The control collagen scaffolds are kept in darkness during the crosslinking process. Fully swollen collagen scaffolds are dehydrated by air-drying on a non-adherent surface for more than 24 hours. Dry collagen membranes are rehydrated in phosphate buffered saline at neutral pH for more than 24 hours and fully swollen collagen membranes of thickness around 100-200 micrometers are obtained for use in subsequent tests. Alternatively, crosslinked collagen scaffolds were freeze-dried to produce porous structures. FIG. 1 shows the magnified view of the cross-section of the collagen scaffolds prepared by this method. Well-organized, laminar-like structures and micr-porous structures are produced.

EXAMPLE 2

Fabrication of Collagen Scaffolds by Lamination of Multiple Layers

Crosslinked dry collagen scaffold prepared by the method of Example 1 is rehydrated in PBS (pH7.4) or water for 30 minutes. The rehydrated collagen membrane prepared as in Example 1 is rinsed in water or other isotonic solution and the water on the surface of the rehydrated scaffolds is removed by blotting dry using kimwipes or other absorbants. The scaffold is carefully laid down at the bottom of a container for reconstitution of collagen gel as described in Example 1. The container has a dimension of 15 mm diameter and approximately 7.5 mm thick. 1.5 ml of degassed acid-soluble rattail collagen solution type I at 4 mg/ml is carefully casted onto the collagen membrane. Any air bubbles generated during this process are removed. The membrane-containing collagen solution is then placed in the ammonia chamber for 30 minutes. Procedures described in Example 1 were repeated to obtain bi-layered crosslinked collagen membranes. The scaffold was dehydrated by air-drying for more than 24 hours. By repeating procedures in Example 1 and 2, collagen scaffolds appropriate thickness can be obtained. For instance, 6- or 10-layer collagen scaffold of approximately 1-2 mm thickness produced by the method disclosed in the present invention can be used for intervertebral disc tissue engineering.

EXAMPLE 3

Mechanical Properties of Collagen Membranes

Figure 2:
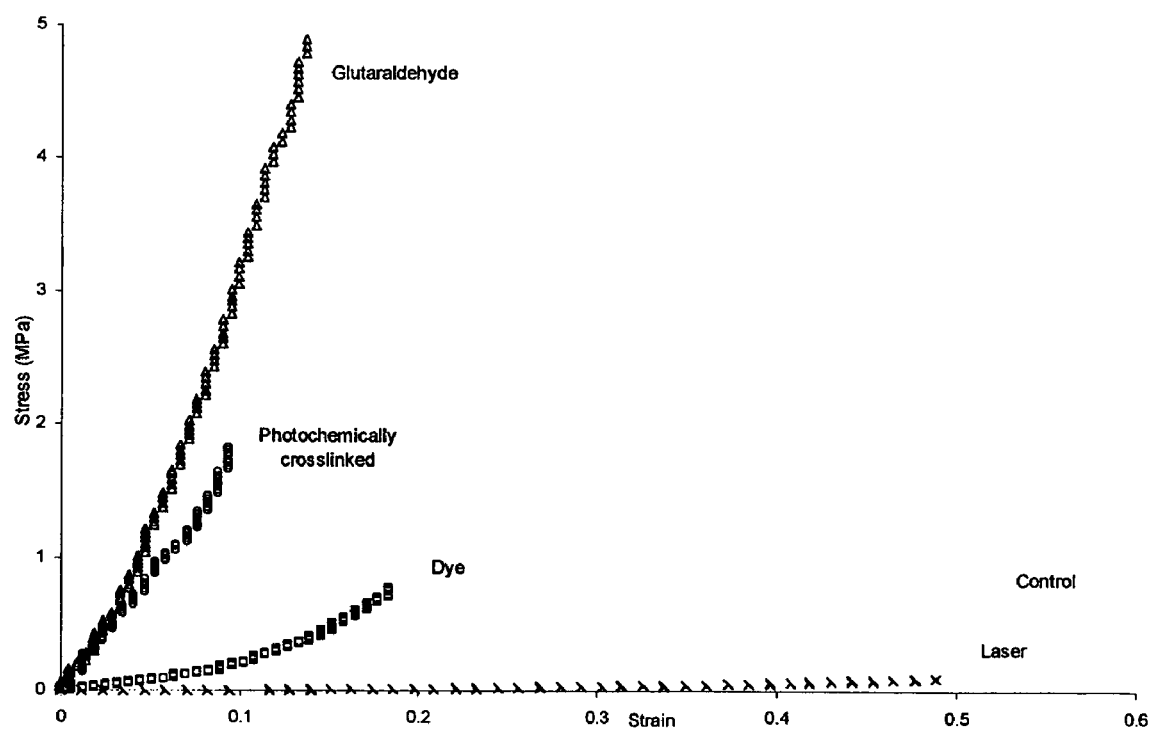
FIG. 2 depicts the representative stress-strain curves of collagen membranes of different treatment groups prepared according to the present invention.
Figure 3:
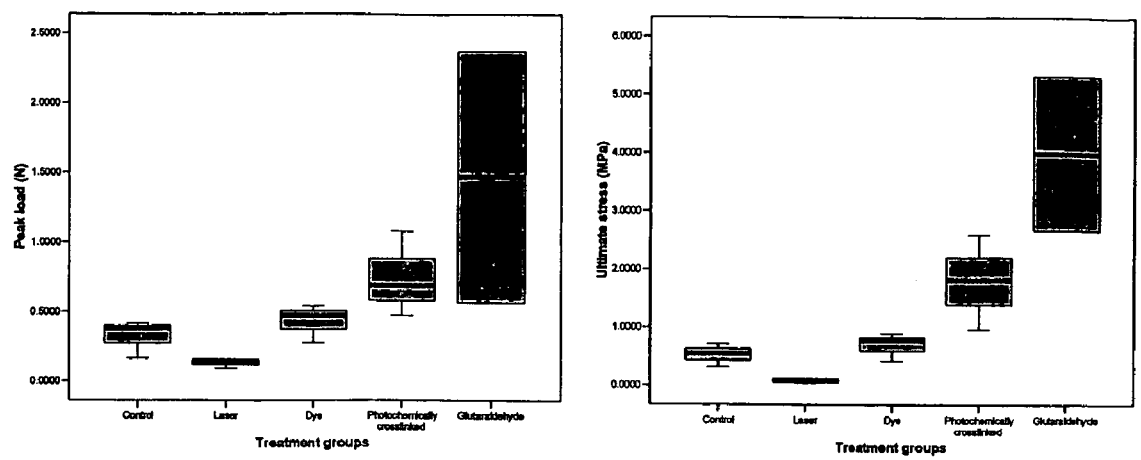
FIG. 3 depicts the peak load (left panel) and ultimate stress (right panel) of collagen membranes of different groups prepared according to the present invention.
Figure 4:
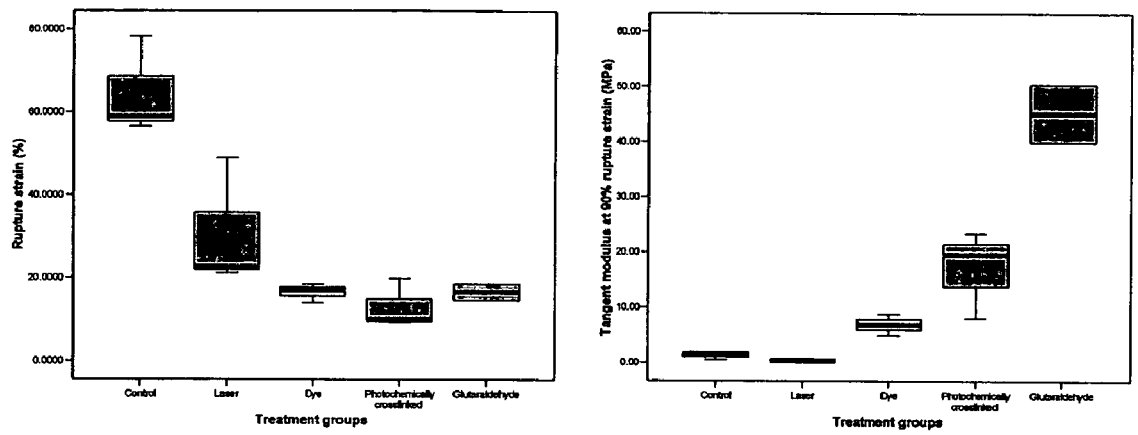
FIG. 4 depicts the rupture strain (left panel) and tangent modulus at 90% of rupture strain (right panel) of collagen membranes of different groups prepared according to the present invention.

Rehydrated collagen membranes as prepared in Example 1 are carved into a dumbbell shape with a gauge length of 0.5 cm, marked with a dye and the width approximately 0.3 cm. The dimension (thickness and width) is measured by a Mitutoyo QUICKVISION PRO system with a precision up to 0.00001 mm. Both ends of the samples are attached with PBS soaked tissue paper and are carefully mounted onto the custom-made fixtures with care. A Lloyd machine attached to a 10N load cell is used to perform the uniaxial tensile test at a strain rate of 5 mm/min. The data acquisition rate is 50 data points per second and the force displacement data are obtained from the machine. A CCTV camera is used to record the tensile process at the samples with a video capture card at a rate of 25 fps. The images were analyzed for strain till rupture (FIG. 4) while the ultimate stress is obtained from the peak force (FIG. 3) and the dimension of the collagen membranes. Stress-strain curve is obtained (FIG. 2) and the tangent modulus at 90% rupture strain is obtained (FIG. 4).

EXAMPLE 4

Thermal Stability of Collagen Membranes

Figure 8:
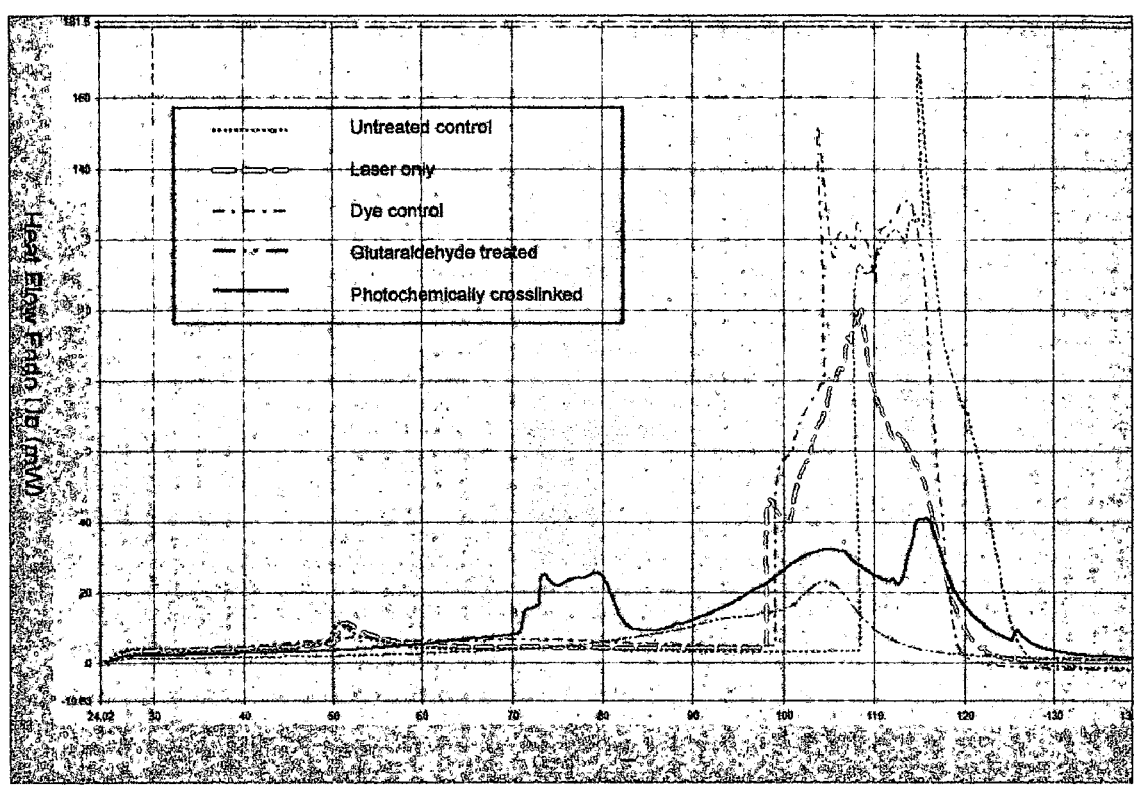
FIG. 8 shows the thermograms of collagen scaffolds of different treatment groups as prepared according to the present invention.
Figure 9:
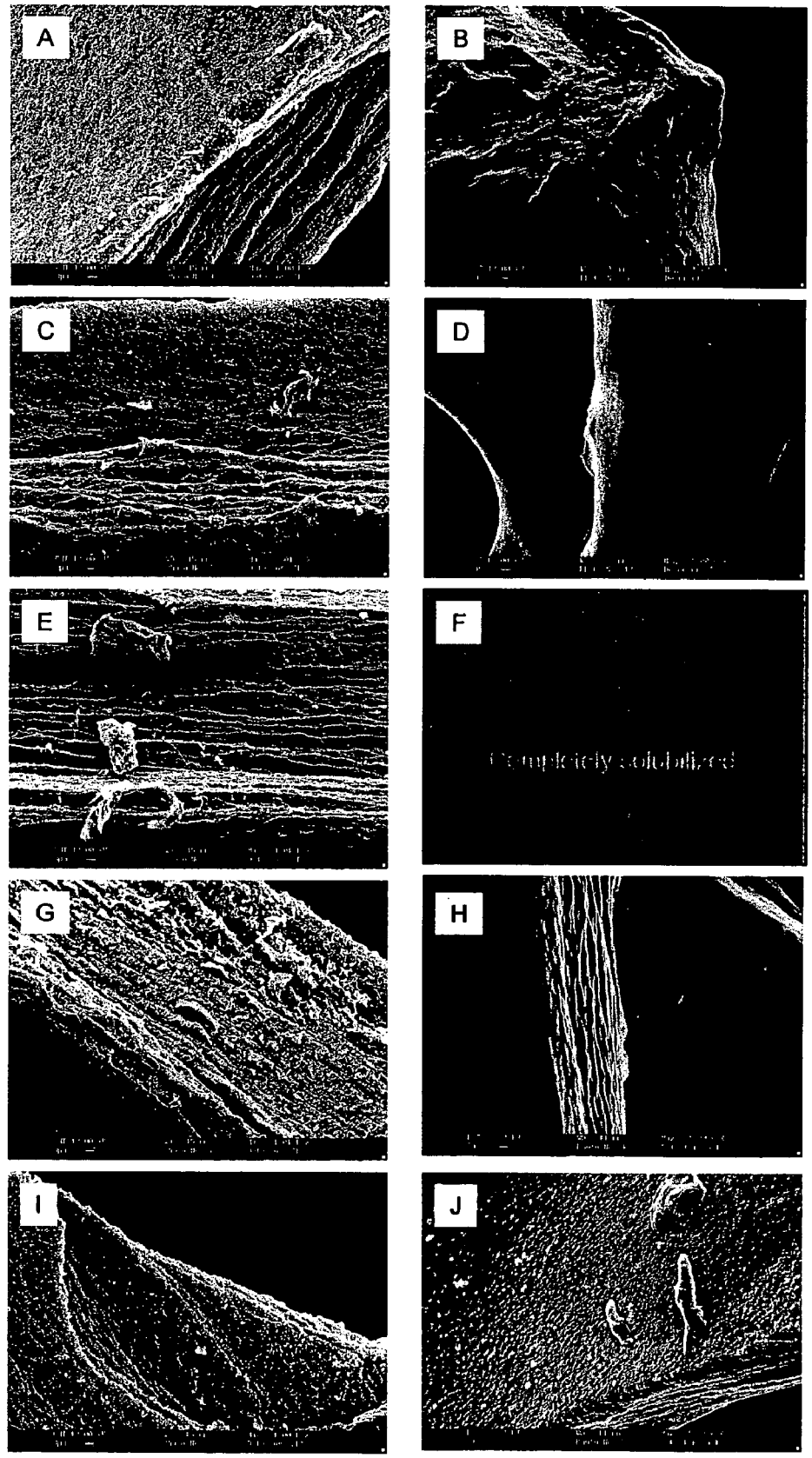
FIG. 9 are magnified (magnification: 1K×) cross-sectional views of the collagen membranes in different treatment groups before (A,C,E,G,I) and after (B,D,F,H,J) thermal stability analysis wherein the three-dimensional structure of the membrane prepared by the method disclosed in the present invention is retained (H) after the thermoscan, similar to the chemically crosslinked (J), whereas the three-dimensional structure of the unprocessed membranes (B,D,F) were not. (A&B: Photochemically crosslinked; C&D: Dye; E&F: Laser (No solid remnant was found and thus no image is available in F); G&H: Control; I&J: Glutaraldehyde.)

Dry collagen membranes are weighed and approximately 1.0-2.5 mg of dry collagen sample is used for differential scanning calorimetry analysis. In brief, the collagen sample is rehydrated in phosphate buffered saline at neutral pH for more than 24 hours at room temperature. Rehydrated samples are cut into small pieces and sealed in an aluminum pan. A thermoscan is performed using a Perkin Elmer DSC7 from 25° C. to 140° C. at a scan rate of 5° C. min, against a reference pan. Thermograms of collagen samples are obtained as shown in FIG. 8 and analyzed using a software Pyris Manager. The shrinkage peak identified as the first endothermic peak from the thermogram is analyzed and the peak temperature is obtained as the shrinkage temperature of the collagen samples in that the intermolecular bonds in particular non-covalent bonding are broken significantly and therefore the samples shrink in volume significantly. At this stage, the collagen membranes are still insoluble or non-denatured. This is confirmed by examining the samples in the aluminum pan after the $1^{st}$ shrinkage peak. However, collagen membranes in all control groups are "melted" or "denatured" as the thermoscan continued and the denaturation completed within a range from 100 to 120° C. On the contrary, photochemically crosslinked collagen membranes prepared by the method disclosed in the present invention and the chemically crosslinked membranes are not "melt" or "denatured" until the end of the thermoscan at 140° C. This is further confirmed by examining the samples inside the aluminum pans post-test. It is found that the control membranes are solubilized while the crosslinked ones were still insoluble. Scanning EM pictures in FIG. 9 showed that the three-dimensional insoluble structures of the rehydrated photochemically crosslinked membrane after the thermoscan while the control membranes were either non-retrievable due to its complete solubility or soft gel like structure without any three-dimensional structure.

EXAMPLE 5

Resistance to Collagenase Digestion of Collagen Membranes

Dehydrated collagen membranes are weighed as $W_1$ and rehydrated in 0.1M Tris-HCl buffer with 5 mM $CaCl_2$ (pH7.4) for more than 24 hrs at room temperature. Collagenase (C-6885, Sigma, 425 U/mg) is prepared to 10 U/ml in the same buffer solution. Collagen membranes are soaked into the collagenase solution at 2 U/mg dry weight and incubated in darkness with regular shaking at 37° C. for 2 hrs. At the end of incubation, an equal volume of 20 mM EDTA (final conc 10 mM) is supplied into the reaction mixture to stop collagenase activity. The supernatant is collected for total protein determination while the remaining membranes are dehydrated using a speed-vac overnight until a constant dry weight $W_2$ is obtained. The weight loss of collagen membranes is calculated as follows and regarded as the resistance to collagenase digestion:

$$\text{Weight loss (\%)} = (W_1 - W_2) \times 100\%$$

Figure 10:
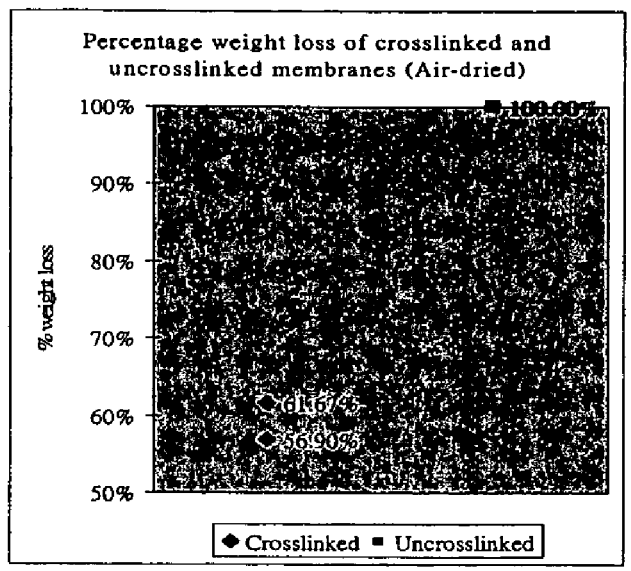
FIG. 10 shows the resistance of the in vitro biodegradability of collagen membranes prepared according to the present invention.

As shown in FIG. 10, the weight loss of the photochemically crosslinked collagen membranes is approximately 60% while the control membranes were all digested by collagenase.

EXAMPLE 6

Temporal Change of the Swelling Ratio of Collagen Membranes and the Dose Dependence of the Energy of Light Collagen membranes with a dry weight ($W_0$) ranging from 2.5 mg to 4 mg are immersed in distilled water in darkness for 0.5, 1, 2, 4, 8, 24, 48, 72 and 96 hours. The wet weights of the membranes are recorded at each time point ($W_t$) after removing the surface water by blotting on kimwipe for several times. The swelling ratio or the water binding capacity of the collagen membranes is calculated as follows:

$$\text{Swelling ratio} = [(W_t - W_0)/W_0]$$

Figure 12:
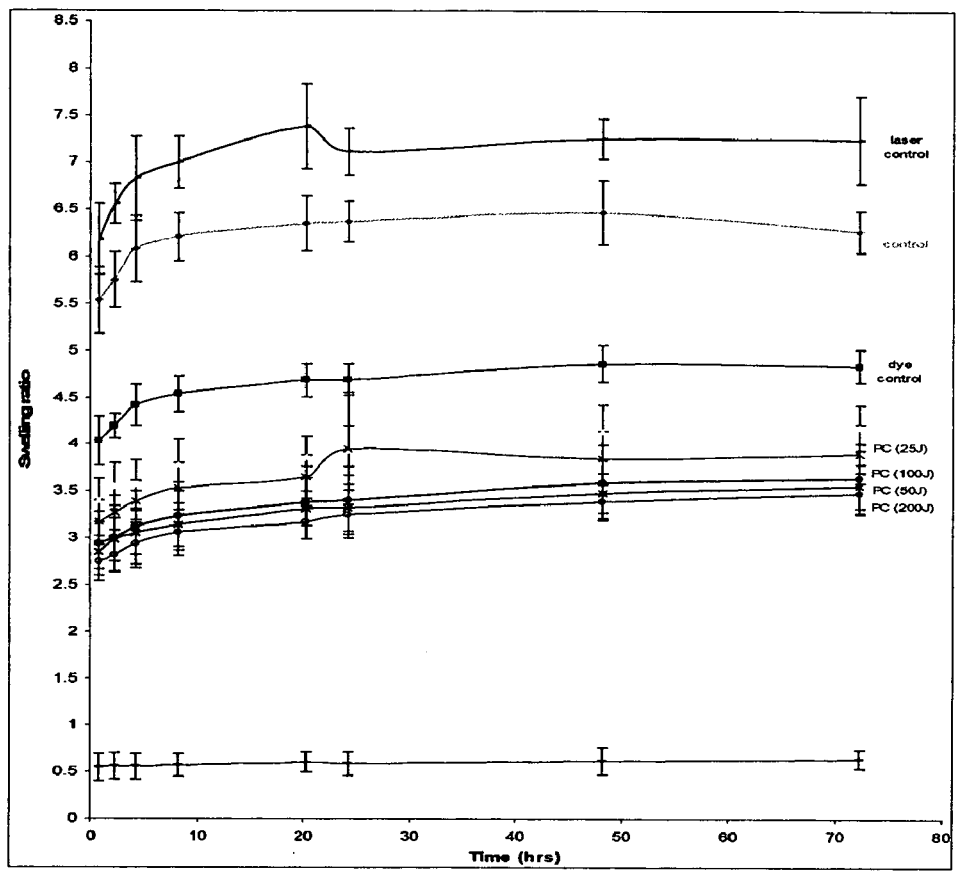
FIG. 12 shows the temporal change in the swelling ratio of collagen membranes prepared in accordance with the present invention and unprocessed membranes and the dose-dependency of the energy of the light source.
Figure 13:
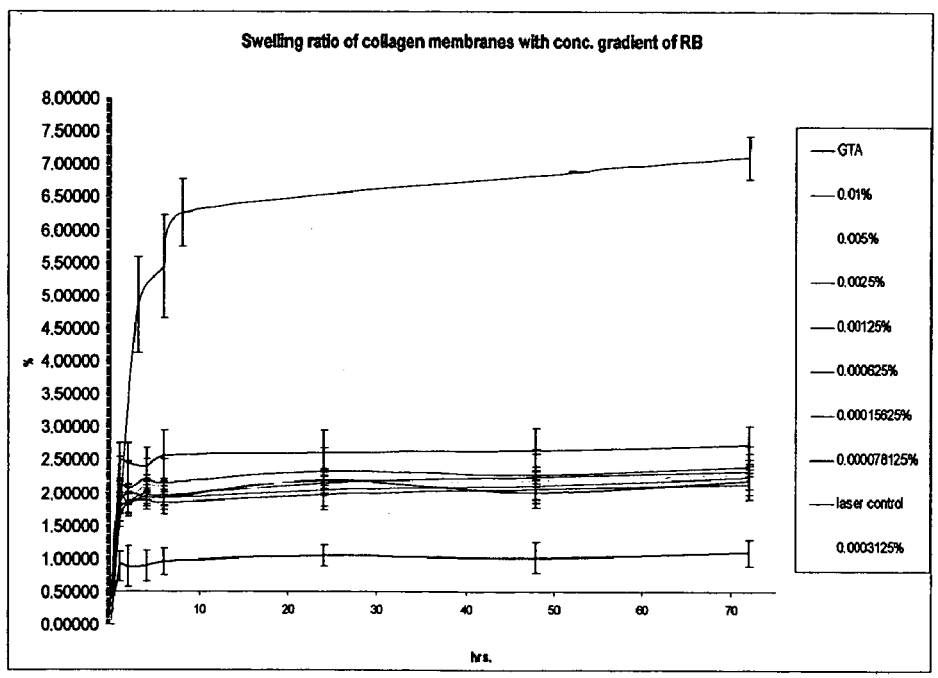
FIG. 13 shows the temporal change in the swelling ratio of collagen membranes prepared in accordance with the present invention and unprocessed membranes and the dose-dependency of the concentration of the photosensitizing reagent.

The swelling ratio of the collagen membranes in different fluence dosage groups against time is plotted in FIG. 12. The control membranes showed the highest swelling ratio ranging approximately from 5.5 to 6.5 initially after swelling and increasing to a constant value ranging from 6 to 7 at the end of the swelling period. Chemically crosslinked collagen membranes using glutaraldehyde have the lowest swelling ratio around 0.5 and were almost non-swelling throughout the swelling period. Photochemically crosslinked collagen membranes at various doses of laser energy (12.5 J to 200 J) and 0.01% photosensitizing reagent show a range of swelling ratio from approximately 2.5 to 4 and increased to values ranged approximately from 3 to 5 at the end of the swelling period. The swelling ratio of the photochemically crosslinked collagen membranes was found to be energy dose-dependent. Dose-dependence on the concentration of photosensitizing dye is shown in FIG. 13.

Swelling is one of the mechanisms for controlled drug release from polymer networks. By controlling the swelling ratio of collagen membranes using the photochemical crosslinking method of the present invention, the release of drugs immobilized in the collagen matrix can be controlled so that a sustained release of the drugs can be attained after implantation of the scaffolds. On the other hand, both the uncrosslinked and chemically crosslinked collagen scaffolds are not suitable for controlled release of drugs because the former release rapidly while the latter permanently bound drugs immobilized in the scaffolds.

EXAMPLE 7

Figure 14:
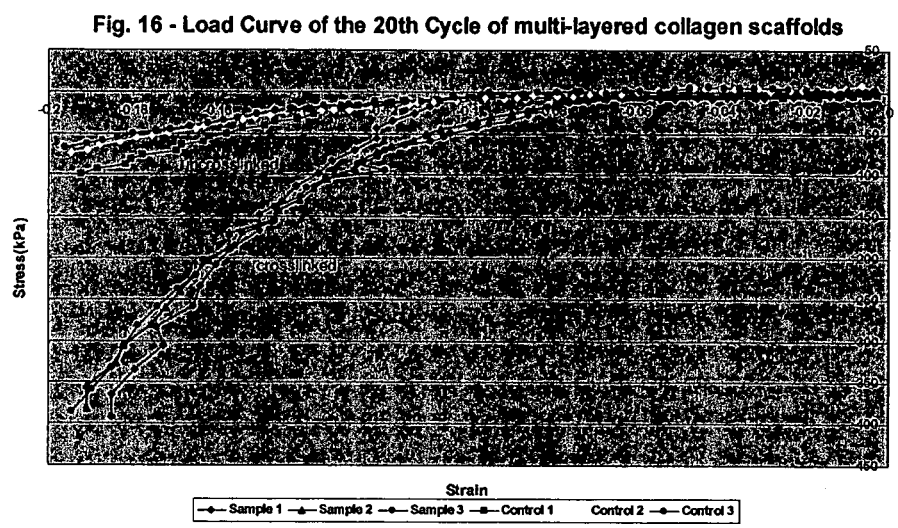
FIG. 14 shows the compression modulus of multi-layered collagen scaffolds prepared in accordance with the present invention.
Figure 15:
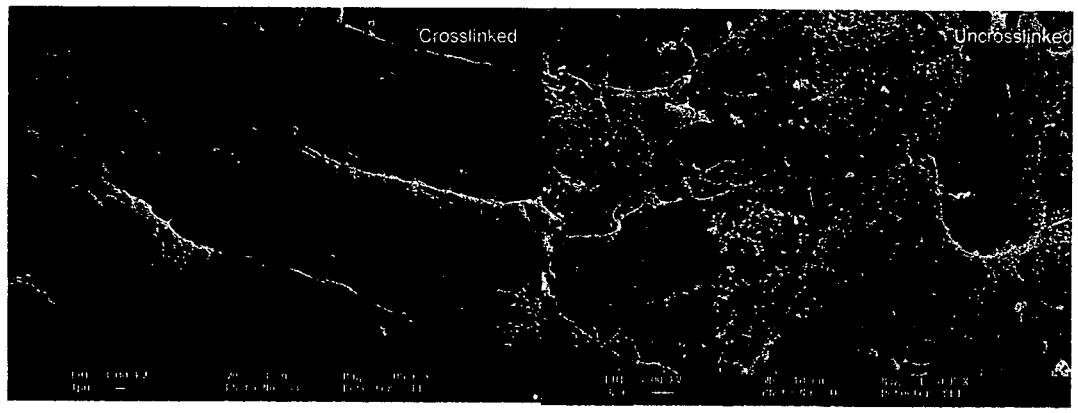
FIG. 15 are magnified view of the surface of crosslinked (2K×) and uncrosslinked (1.7K×) collagen scaffolds to which 3T3 fibroblasts were cultured.

Crosslinked Multi-lamellae Collagen Structures have Greater Dynamic Compression Modulus The multi-lamellae collagen structures made in example 2 have been fully swollen in phosphate buffered saline at pH 7.4 for 2 weeks. Uncrosslinked structures swell extensively to form a soft gel-like structure with a thickness of around 2 mm. The structures were so weak that they can not be manipulated with forceps and sutures can not be put through. On the other hand, structures processed by the methods disclosed here swell moderately to a thickness of around 1 mm and were tough. The structures were then mounted on the sample stage of a MTS Bionix microforce testing machine fitted with a 100N load cell. After preloading with a force of around 0.1N, the strain was set to zero and dynamic compression cycles at a frequency of 0.1 Hz and a maximal strain of 0.5 were conducted. The load and unload-diaplacement curves were evaluated while the curve at the 20th cycle was used for data analysis. The compression moduli normalized by the dimension of the samples were obtained. The stress-strain curves of the uncrosslinked and crosslinked structures were shown in FIG. 14. The modulus for the uncrosslinked ones was minimal while the mean value for the crosslinked was 4.65 Mpa. The values are comparable with that of rat caudal and lumbar discs, with a mean value of 4.03 and 2.16 Mpa, respectively (Elliot & Sarver 2004). Elliott D M, Sarver J J. (2004) Young investigator award winner: validation of the mouse and rat disc as mechanical models of the human lumbar disc. Spine 29(7):713-22. This indicates that the crosslinked scaffolds can be used in engineering weight-bearing tissues.

EXAMPLE 8

Microstructure of Photochemical Crosslinked Scaffolds

Figure 6:
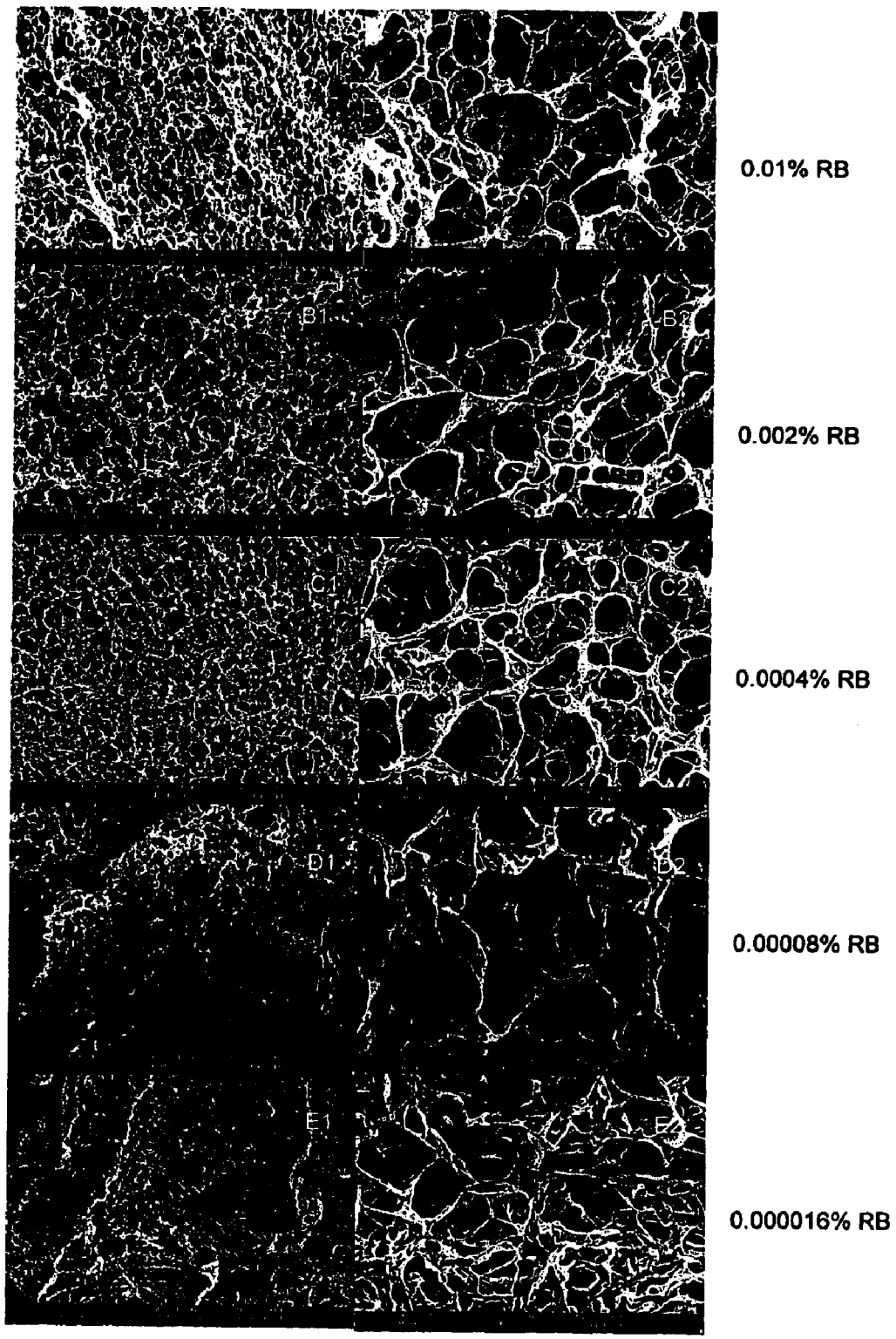
FIG. 6 are magnified cross-sectional views of porous collagen scaffolds treated with different photosensitizing concentrations as prepared according to the present invention. (Magnification: left panel: 2K×; right panel: 8K×.)
Figure 7:
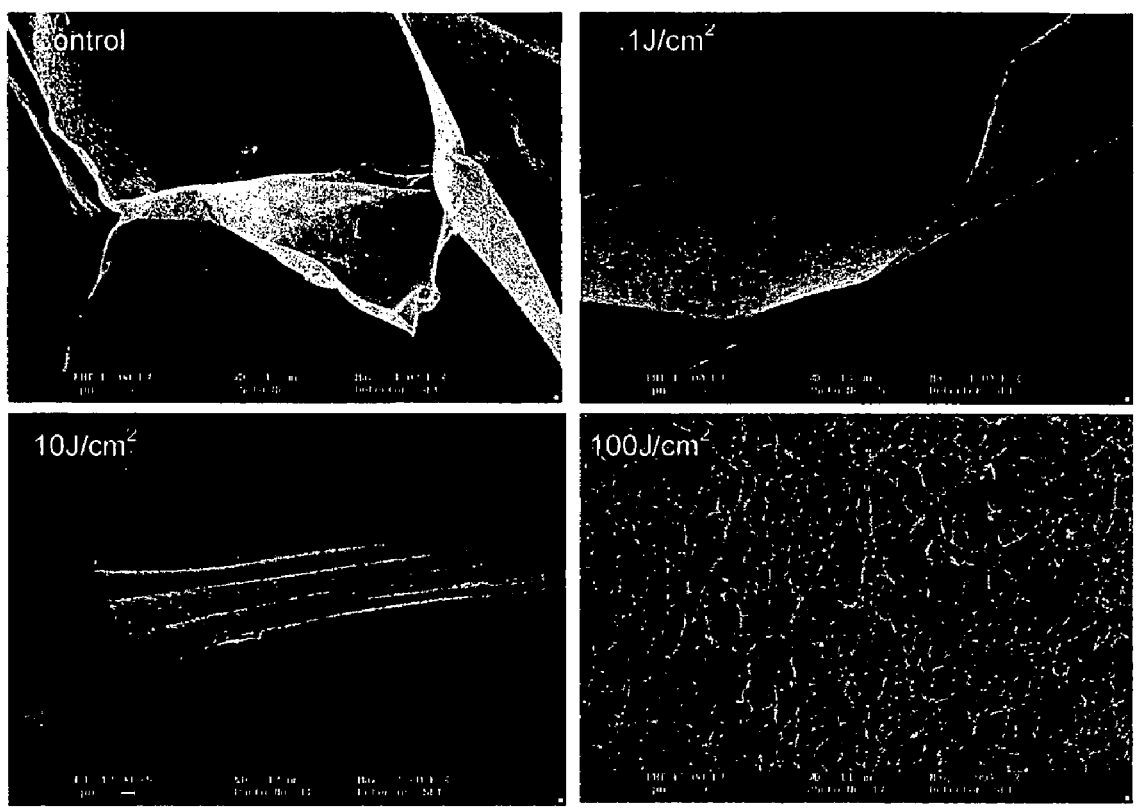
FIG. 7 are magnified cross-sectional views of porous collagen scaffolds crosslinked at different fluence as prepared according to the present invention. (Magnification: 1K×)

Reconstituted collagen gel was photochemically crosslinked by varying the photosensitizing reagent and fluence dosage. Glutaraldyhyde was used as a positive control for chemical crosslinking. The treated structures were freeze-dried. Cross-sections of the collagen scaffolds were sputtered with gold for SEM analysis of the porous structures. FIG. 5 showed that both glutaraldehyde and photochemically collagen scaffolds have fine microstructures with interconnected fibers with nanosized fibers and micro-sized pores. In the control groups, only macrostructures with membrane like structures were found. FIGS. 6 & 7 showed the dose dependent change of microstructures on photosensitizing reagent concentration and fluence, respectively.

EXAMPLE 9

In vivo Biocompatibility by Implantation of Crosslinked Collagen Scaffolds

Figure 11:
FIG. 11 shows the magnified cross-sectional view of collagen membranes prepared according to the present invention implanted in subcutaneous pockets at the back of rats 6 months after implantation. (Magnification: 400×)

Multilayered collagen scaffolds prepared by method in the present invention as illustrated in Example 2 were sterilized by soaking in 70% ethanol for 3 days. Adult SD rats (250 g) were anesthetized and shaved at the back. Subcutaneous pockets were created and the scaffolds were implanted for up to 6 months. The collagen scaffolds were harvested for histological analysis. Collagen scaffolds were completely retrieved and remain intact and covered by a thin (~40 μm) connective tissue capsule. FIG. 11 showed the H&E staining of the scaffolds. Some connective tissue cells wrapped around the edges of the scaffolds and there was no foreign body reaction and inflammation. This showed that the crosslinked structures have excellent biocompatibility and good stability in vivo.

EXAMPLE 10

Reduced Thrombogenicity in Crosslinked Collagen Scaffolds

Figure 16:
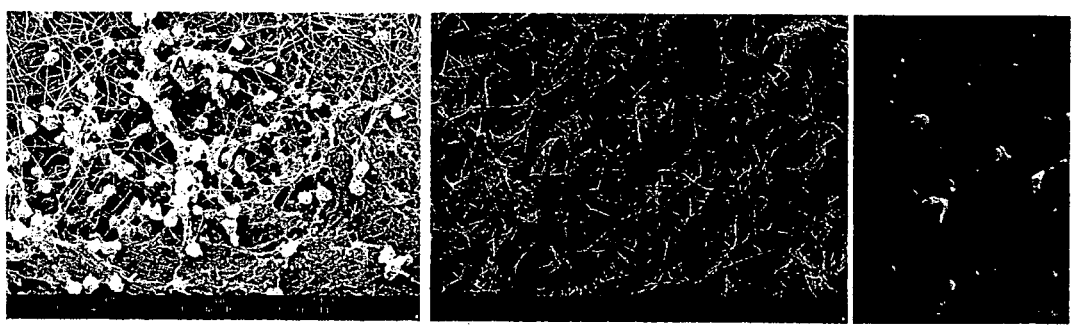
FIG. 16 are magnified views (2K×) of crosslinked and uncrosslinked collagen membranes to which human platelets were attached.

Rattail collagen gel (3 mg/ml) was reconstituted and photochemically crosslinked according to the present invention. Platelet adhesion test using human platelet rich plasma obtained from local blood bank was conducted by incubating the rehydrated membranes with the plasma for 1 hour before thorough rinsing. The samples were fixed in 0.25% glutaraldehyde before processed for SEM analysis. Ten fields were randomly selected from each sample for platelet counts and morphology analysis. Uncrosslinked collagen membranes have intrinsic thrombogenicity that more platelets adhered to the surface (57±28 per unit area) (FIG. 16A) and extensive fibrin mesh activation was found (FIG. 16B). On the contrary, photochemical crosslinked collagen membranes significantly reduced the extent of platelet adhesion (FIG. 16C) for as much as 6 fold (9.5±3 per unit area) and completely aborted thrombin activation. This study suggested that photochemical crosslinking can be used as a processing technique to reduce thrombogenecity of biomaterials such as collagen in engineering artificial blood vessels.

INDUSTRIAL APPLICABILITY

1. Manufacturers of biomaterials e.g. collagen, can incorporate the processing technology of the present invention into their own manufacturing processes so that their products will have better mechanical and material properties, swelling capacity and resistance to enzymatic digestion. The products so produced are useful in both tissue engineering research and in clinical applications.
2. Companies that manufacture products for engineered tissues can incorporate the present method into their manufacturing process to obtain better products.
3. Drug delivery companies can incorporate the present process into their manufacturing processes so as to develop new carriers for drugs with improved stability and controlled release properties due to an increased resistance to collagenase digestion and decreased swelling ratio.
4. Light source companies such as laser companies can develop suitable light sources for the processing technology.

The invention claimed is:
1. A method for producing a crosslinked collagen scaffold comprising (a) providing a solution of extracellular collagen monomers at an acidic pH; (b) raising the pH of the solution to form a reconstituted three-dimensional extracellular collagen matrix; (c) contacting at least a portion of the reconstituted three-dimensional extracellular collagen matrix with a photoactivating reagent; (d) removing excess photoactivating reagent; (e) irradiating the reconstituted three-dimensional extracellular collagen matrix, in a hydrated state without bubbling air or oxygen into the reaction mixture or vigorous stirring, using a source of light of sufficient energy to form a crosslinked scaffold; and (f) dehydrating the crosslinked scaffold.

2. The method of claim 1, further comprising (g) rehydrating the crosslinked scaffold; and (h) laminating the crosslinked scaffold by applying the solution of extracellular collagen monomers at an acidic pH onto the crosslinked scaffold and repeating steps (b) through (f).

3. The method of claim 1 wherein the extracellular collagen monomers are selected from the group consisting of collagen type I, collagen type II, and collagen type III.

4. The method of claim 3 wherein the collagen is isolated from human tissue.

5. The method of claim 1 wherein the extracellular collagen monomers are obtained from rat tail, bovine Achilles tendon, porcine skin, or human placenta.

6. The method of claim 1 wherein the extracellular collagen monomers are from fractions of collagen extracted from animal sources, wherein the fractions of collagen are selected from the group consisting of acid-soluble fractions and pepsin digested fractions.

7. The method of claim 1 wherein raising the pH of the collagen monomer solution comprises exposing the solution in a chamber filled with an alkaline vapor or alkaline solution for a period ranging from 3 minutes to 96 hours.

8. The method of claim 1 wherein raising the pH of the collagen monomer solution comprises exposing the collagen monomer solution to an alkaline solution through a semipermeable membrane or its equivalent.

9. The method of claim 8 wherein the exposing the collagen monomer solution to an alkaline solution through a semipermeable membrane is done by sealing the collagen monomer solution in a dialysis tubing or cellulose membrane and immersing the dialysis tubing or cellulose membrane in the alkaline solution.

10. The method of claim 9 wherein the alkaline solution is aqueous ammonia.

11. The method of claim 1 wherein the photoactivating reagent is selected from the group consisting of fluorescein, rose Bengal, methylene blue, eosin, and a porphyrin.

12. The method of claim 1 wherein the photoactivating reagent has a concentration ranging from 0.00001% to 1% (w/v).

13. The method of claim 1 wherein the reconstituted three-dimensional extracellular collagen matrix is brought into contact with the photoactivating reagent after reconstitution for a period ranging from 5 seconds to 100 hours.

14. The method of claim 1 wherein the excess photoactivating reagent is removed by multiple rinses in water or an isotonic solution.

15. The method of claim 1 wherein the source of light is a UV or visible light source.

16. The method of claim 1 wherein the source of light irradiates the reconstituted three-dimensional extracellular collagen matrix at an irradiance ranging from 0.0001 W/cm$^2$ to 10 W/cm$^2$.

17. The method in claim 1 wherein the source of light irradiates the reconstituted three-dimensional extracellular collagen matrix in a pulsed or continuous manner.

18. The method of claim 1 wherein the source of light has an irradiation energy ranging from 0.0001 J to 10000 J.

19. The method of claim 1 wherein the irradiating is done for a period ranging from 3 seconds to 100 hours.

20. The method of claim 1, wherein step (e) further comprises cooling the crosslinked scaffold in a container equipped with cooling means.

21. The method of claim 20 wherein the cooling means is cold water or air.

22. The method of claim 1 wherein the dehydrating the crosslinked scaffold is carried out by air-drying, freeze-drying, vacuum drying, critical point drying, alcohol drying, or acetone drying.

23. The method of claim 7, wherein the alkaline vapor is ammonia vapor.

24. The method of claim 1 wherein the source of light is a laser, an argon laser, a xenon light, or a light-emitting diode (LED).

25. A method for producing a crosslinked collagen scaffold comprising (a) providing a solution of extracellular collagen monomers at an acidic pH; (b) raising the pH of the solution by exposing the solution in a chamber filled with ammonia vapor to form a reconstituted three-dimensional extracellular collagen matrix; (c) contacting at least a portion of the reconstituted three-dimensional extracellular collagen matrix with rose Bengal; (d) removing excess rose Bengal; (e) irradiating the reconstituted three-dimensional extracellular collagen matrix using an argon laser to form a crosslinked scaffold; and (f) dehydrating the crosslinked scaffold.

26. The method of claim 25 further comprising (g) rehydrating the crosslinked scaffold of step (f); and (h) laminating the crosslinked scaffold of step (g) by applying the solution of extracellular collagen monomers at an acidic pH onto the crosslinked scaffold and repeating steps (b) through (f).

* * * * *